United States Patent [19]
Deubzer et al.

[11] Patent Number: 5,994,490
[45] Date of Patent: Nov. 30, 1999

[54] PROCESS FOR EQUILIBRATING AND/OR CONDENSING ORGANOSILICON COMPOUNDS

[75] Inventors: Bernward Deubzer, Burghausen; Christian Herzig, Waging am See, both of Germany

[73] Assignee: Wacker-Chemie GmbH, Munich, Germany

[21] Appl. No.: 09/067,871

[22] Filed: Apr. 28, 1998

[51] Int. Cl.$^6$ ..................................................... C08G 77/06
[52] U.S. Cl. ............................................. 528/23; 502/167
[58] Field of Search ................................ 528/23; 502/167

[56] References Cited

U.S. PATENT DOCUMENTS

| | | |
|---|---|---|
| 5,380,902 | 1/1995 | Hager et al. . |
| 5,403,909 | 4/1995 | Rubinsztajn . |
| 5,420,221 | 5/1995 | Razzano et al. ........................ 528/23 |
| 5,424,385 | 6/1995 | Hager et al. . |
| 5,621,061 | 4/1997 | Hager et al. ............................ 528/23 |

FOREIGN PATENT DOCUMENTS 0626414  11/1994  European Pat. Off. .

*Primary Examiner*—Melvyn I. Marquis
*Attorney, Agent, or Firm*—Brooks & Kushman P.C.

[57] ABSTRACT

Compositions obtained by mixing oxygen-containing phosphazenes with tertiary alcohols at a temperature of from 0° C. to 70° C. and a pressure of from 900 to 1100 hPa are useful in processes for equilibrating and/or condensing organosilicon compounds.

10 Claims, No Drawings

PROCESS FOR EQUILIBRATING AND/OR CONDENSING ORGANOSILICON COMPOUNDS

TECHNICAL FIELD

The invention relates to compositions derived from oxygen-containing phosphazenes and tertiary alcohols, to a method of preparing them, and to their use in a process for preparing organopolysiloxanes by equilibration and/or condensation reactions.

BACKGROUND ART

For the purposes of the present invention, the term organopolysiloxanes also encompasses oligomeric siloxanes.

The preparation of organopolysiloxanes by equilibration and/or condensation reactions in the presence of oxygen-containing phosphazenes is already known and described, for example, in U.S. Pat. No. 5,380,902 (Wacker-Chemie GmbH; published on Jan. 10, 1995). U.S. Pat. No. 5,403,909 (General Electric Co.; published on Apr. 4, 1995) and the corresponding DE-A 44 23 924 describe the reaction product of an oxygen-containing phosphazene catalyst with a compound containing at least one active proton having a pKa of less than 18, for example a primary or secondary alcohol, but this generally leads to elimination of hydrogen chloride, dark discoloration, precipitates and a decrease in activity.

SUMMARY OF THE INVENTION

The present invention provides compositions obtained by mixing oxygen-containing phosphazenes with tertiary alcohols at temperatures which preferably range from 0 to 70° C. and pressures which preferably range from 900 to 1100 hPa.

DESCRIPTION OF THE PREFERRED EMBODIMENT

The compositions of the invention can be prepared by mixing oxygen-containing phosphazenes and tertiary alcohols in any manner. Thus, for example, it is possible to initially charge a tertiary alcohol or a mixture of various tertiary alcohols and to add the amount of oxygen-containing phosphazenes necessary to achieve the desired concentration or, conversely, tertiary alcohol or a mixture of various tertiary alcohols can be added to oxygen-containing phosphazenes.

The compositions of the invention are prepared according to the invention at temperatures of from 0 to 70° C., preferably from 0 to 40° C., particularly preferably from 0 to 20° C., and generally at the pressure of the surrounding atmosphere, i.e. from 900 to 1100 hPa. In any case, it has to be ensured that the heat of reaction is dissipated by appropriate measures, e.g. slow addition and/or cooling, so that the temperature of the preparation obtained according to the invention does not exceed 70° C., and preferably does not exceed 40° C.

The invention further provides a process for preparing compositions derived from oxygen-containing phosphazenes and tertiary alcohols by mixing oxygen-containing phosphazenes and tertiary alcohols at a temperature of from 0 to 70° C. and a pressure of from 900 to 1100 hPa. The process of the invention is preferably carried out in an atmosphere which is substantially free of oxygen or water, for example in a nitrogen, argon or carbon dioxide atmosphere, with preference being given to a nitrogen atmosphere.

To prepare the compositions of the invention, the weight ratio of oxygen-containing phosphazene used to tertiary alcohol used is preferably from 1:10 to 1:0.5, particularly preferably from 1:5 to 1:1.

The oxygen-containing phosphazenes used according to the invention can be any previously known oxygen-containing phosphazenes. On this subject, reference may be made, for example, to U.S. Pat. No. 5,380,902 as mentioned at the outset and also the literature cited therein, viz. J. Emsley et al., J. Chem. Soc. A (1971), p. 2863 ff, H. R. Allcock et al. in J. Am. Chem. Soc. 107 (1985) p. 5167 ff and R. De Jaeger et al., Macromolecules 25 (1992) p. 1254 ff.

The oxygen-containing phosphazenes used according to the invention are preferably phosphazenes of the formula $$Y-PCl_2=N(-PCl_2=N)_n-PCl_2O \quad (I)$$

where

Y is a chlorine atom or hydroxyl group and n is 0 or an integer from 1 to 8, preferably 0 or an integer from 1 to 4, particularly preferably from 1 to 3, and/or their condensation products.

When Y is a hydroxyl group, the following tautomerism exists $$HO-PCl_2=N(-PCl_2=N)_n-PCl_2O \iff \quad (I)$$

$$O=PCl_2-NH(-PCl_2=N)_n-PCl_2O \quad (I')$$

where n is as defined above. In general, at a pH <7 the equilibrium tends to lie on the left, i.e. favoring compound (I), and at a pH >7 the equilibrium tends to lie on the right, i.e. favoring compound (I').

Furthermore, when Y is a hydroxyl group and the phosphazene has more than three phosphorus atoms, there are further resonance structures in respect of the inner chain members, e.g.

$$HO-PCl_2=N(-PCl_2=N)_2-PCl_2 \iff \quad (I)$$

$$O=PCl_2-NH(-PCl_2=N)_2-PCl_2O \quad (I')$$

$$O=PCl_2-N=PCl_2-NH-PCl_2=N-PCl_2=O \quad (I'')$$

All statements regarding compounds of the formula (I) where Y is OH therefore also apply without restriction to tautomeric compounds such as those of the formulae (I') and (I'').

Although not shown in formula (I), the chlorine atoms can be replaced completely or partly by radicals Q, where Q is, for example, a hydroxyl group, a monovalent organic radical such as an alkoxy radical or aryloxy radical, a halogen atom different from chlorine, an organosilicon radical or a phosphorus- containing radical.

The oxygen-containing chlorophosphazenes of the formula (I) are preferably ones in which none of the chlorine atoms are replaced by a radical Q.

The condensation products according to the present invention of the oxygen-containing chlorophosphazenes of the formula (I) can be any condensation products. For example, if the condensation process takes place at the terminal phosphorus atoms of two oxygen-containing chlorophosphazenes by elimination of HCl or water, the condensation products obtained are oxygen-containing phosphazenes of the formula (I) in which Y is —O—PCl$_2$=N(—PCl$_2$=N)$_n$—PCl$_2$O and n is as defined above. Condensation reactions on non-terminal phosphorus atoms, particularly when at least one chlorine atom in the formula (I) is replaced by a radical Q=hydroxyl, give oxygen-containing phosphazenes of the formula (I) in which Q is a phosphorus-containing radical such as —N=P≡ and

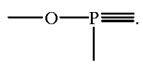

Examples of the oxygen-containing chloro-phosphazenes used according to the invention are $PCl_3=N-PCl_2O$, $PCl_3=N-PMeClO$, $PCl_3=N-P(OPh)_2O$, $PCl_3=N-PMe(OPh)O$, $PCl_3=N-PEt_2O$, $PCl_3=N-PCl_2=N-PCl_2O$, $PCl_3=N(-PCl_2=N)_2-PCl_2O$, $PCl_3=N(-PCl_2=N)_3-PCl_2O$, $PCl_3=N(-PCl_2=N)_4-PCl_2O$, $PCl_3=N(-PCl_2=N)_5,-PCl_2O$, $PCl_3=N(-PCl_2=N)_6-PCl_2O$, $PCl_3=N-PCl(N=PCl_3)-PCl_2O$, $PCl_3=N-P(N=PCl_3)_2-PCl_2O$, $HO-PCl_2=N-PCl_2O$, $HO-PCl_2=N-P(OPh)_2O$, $HO-PPh_2=N-PCl_2O$, $HO-PCl_2=N-PEt_2O$, $HO-PCl_2=N-PCl_2=N-PCl_2O$, $HO-PCl_2=N(-PCl_2=N)_2-PCl_2O$, $HO-PCl_2=N(-PCl_2=N)_3-PCl_2O$, $HO-PCl_2=N(-PCl_2=N)_4-PCl_2O$, $HO-PCl_2=N(-PCl_2=N)_5-PCl_2O$, $HO-PCl_2=N(-PCl_2=N)_6-PCl_2O$, $HO-PCl_2=N-PCl(N=PCl_3)-PCl_2O$, $HO-PCl_2=N-P(N=PCl_3)_2-PCl_2O$, $HO-PCl_2=N-PCl(OH)=N-PCl_2O$, $HO-PCl_2=N-PCl_2=N-PCl(OH)=N-PCl_2O$, $HO-PCl_2=N-P(N=PCl_2OH)(N=PCl_3)-PCl_2O$, $OPCl_2=N-PCl_2-O-PCl_2=N-PCl_2O$, $OPCl_2(-N=PCl_2)_2-O-(PCl_2=N-)_2PCl_2O$, $OPCl_2(-N=PCl2)_3-O-(PCl_2=N-)_3PCl_2O$, $HO-PCl(OBu)=N-PCl(OBu)=N-PCl(OBu)O$, $HO-PCl(OPh)=N-PCl(OPh)=N-PCl(OPh)O$, $HO-PCl_2=N-PCl(OPCl_2=N-PCl_2O)=N-PCl_2O$ and $HO-PCl_2=N-PCl_2=N-PCl(OSiMe_2[OSiMe_2]_{10}OH)=N-PCl_2O$, with preference being given to using $PCl_3=N-PCl_2O$, $PCl_3=N-PCl_2=N-PCl_2O$, $PCl_3=N(-PCl_2=N)_2-PCl_2O$, $PCl_3=N(-PCl_2=N)_3-PCl_2O$, $PCl_3=N(-PCl_2=N)_4-PCl_2O$, $HO-PCl_2=N-PCl_2O$, $HO-PCl_2=N-PCl_2=N-PCl_2O$, $HO-PCl_2=N(-PCl_2=N)_2-PCl_2O$, $HO-PCl_2=N(-PCl_2=N)_3-PCl_2O$, $HO-PCl_2=N(-PCl_2=N)_4-PCl_2O$, $OPCl_2=N-PCl_2-O-PCl_2=N-PCl_2O$, $OPCl_2(-N=PCl_2)_2-O-(PCl_2=N-)_2PCl_2O$ and $OPCl_2(-N=PCl_2)_3-O-(PCl_2=N-)_3PCl_2O$, particularly preferably $PCl_3=N-PCl_2=N-PCl_2O$, $PCl_3=N(-PCl_2=N)_2-PCl_2O$, $PCl_3=N(-PCl_2=N)_3-PCl_2O$, $HO-PCl_2=N-PCl_2=N-PCl_2O$, $HO-PCl_2=N(-PCl_2=N)_2-PCl_2O$ and $HO-PCl_2=N(-PCl_2=N)_3-PCl_2O$. In these formulae, Me=methyl, Et=ethyl, Bu=n-butyl and Ph=phenyl.

The oxygen-containing phosphazenes can be prepared by methods known in chemistry, for instance as described in the above-mentioned references. For example, oxygen-containing phosphazenes can be prepared by reacting ionic phosphazenes with hydroxyl-containing compounds.

The tertiary alcohols used in the process of the invention for preparing the compositions of the invention are alcohols in which the hydroxyl group is bound to a tertiary carbon atom, i.e. a carbon atom which is bound directly to three further carbon atoms.

The tertiary alcohols used according to the invention are preferably tertiary alcohols having a pKa of greater than or equal to 18.

Examples of tertiary alcohols used according to the invention are tertiary butanol, 1,1-dimethyl-l-propanol, 2,3-dimethyl-2-butanol, 2,3-dimethyl-2-pentanol, 1-methylcyclohexanol, 1-methylcyclopentanol, 2-methyl-2-hexanol, 2-methyl-2-pentanol, 2-methyl-4-trimethylsilyl-2-butanol, 2-methyl-4-dimethyl-phenylsilyl-2-butanol and 2-phenyl-2-propanol. If only for reasons of safety in handling, preference is given to using tertiary alcohols having a boiling point at the pressure of the surrounding atmosphere, i.e. from 900 to 1100 hPa, of over 100°C., for example 1,1-dimethyl-1-propanol (tertiary amyl alcohol).

The components employed for preparing the compositions according to the invention can in each case be one type of such a component or else a mixture of at least two types of a respective component.

The process of the invention has the advantage that the compositions of the invention can be prepared in a simple way. Furthermore, the process of the invention has the advantage that only very small amounts of free hydrogen chloride are produced and the reaction of the components proceeds in a readily controllable manner.

The compositions of the invention can be used wherever phosphazenes have also been used hitherto. In particular, they are suitable as catalysts in processes for equilibrating and/or condensing organosilicon compounds.

The invention further provides a process for equilibrating and/or condensing organosilicon compounds in the presence of the novel compositions derived from oxygen-containing phosphazenes and tertiary alcohols.

In the process of the invention for equilibrating and/or condensing organosilicon compounds, the amounts of compositions derived from oxygen-containing phosphazenes and tertiary alcohol which may be employed according to the present invention can be, based on the phosphazenes, the same as those employed in the previously known processes for preparing organosilicon compounds by equilibration and/or condensation. However, owing to the high effectiveness of the compositions derived from oxygen-containing phosphazenes and tertiary alcohol, lower amounts than those used in previously known processes are generally quite sufficient.

The compositions derived from oxygen-containing chlorophosphazenes and tertiary alcohol which are active as catalysts for promoting equilibration and/or condensation reactions of organosilicon compounds are preferably used in amounts of from 0.1 to 1000 ppm by weight (parts by weight per million parts by weight), particularly preferably from 1 to 300 ppm by weight, based on the total weight of the organosilicon compounds to be equilibrated and/or condensed.

In the process of the invention, the compositions derived from oxygen-containing phosphazenes and tertiary alcohol can be used as pure substances, particularly when they are liquid. However, they can also be used in admixture with materials which do not react with the compositions derived from oxygen-containing chlorophosphazenes and tertiary alcohol, although this is not preferred. Thus, in the process of the invention, the novel compositions derived from oxygen-containing chlorophosphazenes and tertiary alcohol can be used in admixture with halogen-free organic solvents, excluding tertiary alcohols, with preference being given to solvents or solvent mixtures having a boiling point or boiling range at atmospheric pressure of up to 160° C., in particular up to 120° C.

Examples of such solvents are ethers such as dioxane, tetrahydrofuran, diethyl ether and diethylene glycol dimethyl ether; esters such as methyl acetate, ethyl acetate, n-propyl and iso-propyl acetates, diethyl carbonate and ethyl formate; hydrocarbons such as pentane, n-hexane, hexane isomer mixtures, cyclohexane, heptane, octane, naphtha, petroleum ether, benzene, toluene and xylenes; ketones such as acetone, methyl ethyl ketone, diethyl ketone, and methyl isobutyl ketone; amides such as dimethylformamide and N-methyl-pyrrolidone; and also mixtures of these solvents, with particular preference being given to hydrocarbons, in particular toluene and xylenes, and esters, in particular ethyl acetate.

If, in the process of the invention, the compositions derived from oxygen-containing phosphazenes and tertiary alcohol are used in admixture with halogen-free organic solvents, with the exception of tertiary alcohols, the concentration of the composition used according to the invention is preferably from 0.01 to 50% by weight, particularly preferably from 0.1 to 20% by weight, based on the weight of the mixture.

If desired, the compositions derived from oxygen-containing phosphazenes and tertiary alcohol and used according to the present invention can, of course, also be used in admixture with halogen-containing solvents, but this is usually not desirable, particularly from the point of view of toxicity.

In the process of the invention, the organo-silicon compounds used can be any organosilicon compounds which have hitherto also been able to be eguilibrated and/or condensed in the presence of catalysts based on phosphazene.

Condensation reactions of organosilicon compounds are, in particular, the reactions of two Si-bonded hydroxyl groups with elimination of water, also, for example, the reaction of an Si-bonded hydroxyl group with an Si-bonded alkoxy group with elimination of alcohol or with Si-bonded halogen with elimination of hydrogen halide. For the purposes of the present invention, equilibration reactions are the rearrangements of siloxane bonds in siloxane units. One or more siloxane units of the same or different viscosity in any mixing ratios can be subjected to the equilibration reaction with or without changing the viscosity of the equilibration product and with or without achieving the equilibrium concentration of cyclic polysiloxanes in the equilibration product. Equilibration and condensation reactions frequently proceed simultaneously. The process of the invention preferably concerns equilibration reactions.

Organosilicon compounds which can be used in the process of the invention are generally known and frequently have the formulae $$X(SiR_2O)_aSiR_2X \qquad (II)$$

and $$(SiR_2O)_b \qquad (III)$$

where R can be identical or different and are each a hydrogen atom or a monovalent, substituted or unsubstituted hydrocarbon radical, X can be identical or different and are each a hydroxyl group, a radical —OR$^1$ where R$^1$ is a monovalent organic radical, —OSiR$_3$ where R is as defined above or a halogen atom, a is 0 or an integer which is at least 1, preferably from 2 to 1000, particularly preferably from 2 to 500, and b is an integer from 3 to 12, preferably from 4 to 8, particularly preferably 4.

Although not shown by the usual formulae, up to 5 mol % of the diorganosiloxane units can be replaced by other siloxane units such as RSiO$_{3/2}$ and/or SiO$_{4/2}$ units, where R is as defined above. Furthermore, in the formulae shown, up to 10 mol % of the diorganosiloxane units can be replaced by carbosiloxy units as are described in DE-A 39 14 896, DE-A 41 23 423 and DE-A 195 22 144.

The radical R is preferably a hydrogen atom or a hydrocarbon radical having from 1 to 18 carbon atoms, with particular preference being given to hydrocarbon radicals having from 1 to 4 carbon atoms, in particular the methyl radical.

Examples of radicals R are alkyl radicals such as the methyl, ethyl, n-propyl, iso-propyl, n-butyl, iso-butyl, tert-butyl, n-pentyl, iso-pentyl, neo-pentyl and tert-pentyl radicals, hexyl radicals such as the n-hexyl radical, heptyl radicals such as the n-heptyl radical, octyl radicals such as the n-octyl radical and iso-octyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical; alkenyl radicals such as the vinyl, allyl, n-5-hexenyl, 4-vinylcyclohexyl and 3-norbonenyl radicals; cycloalkyl radicals such as cyclopentyl, cyclohexyl, 4-ethylcyclo-hexyl, cycloyheptyl, norbornyl and methylcyclohexyl radicals; aryl radicals such as the phenyl, biphenyl, naphthyl, anthryl and phenanthryl radicals, alkaryl radicals such as o—, m—, p-tolyl radicals, xylyl radicals and ethylphenyl radicals; aralkyl radicals such as the benzyl radical, the α and β-phenylethyl radical.

Examples of monovalent, substituted hydrocarbon radicals R are cyanoalkyl radicals such as the βcyanoethyl radical, haloalkyl radicals such as the 3,3,3-trifluoropropyl radical and the γ-chloropropyl radical, haloaryl radicals such as o—, m—and p-chlorophenyl radicals; the 3-hydroxypropyl radical, acyloxyalkyl radicals such as the γ-acryloxypropyl radical and the γ-methacryloxypropyl radical.

The radical R$^1$ is preferably an alkyl radical having from 1 to 4 carbon atoms, particularly preferably a methyl or ethyl radical.

The viscosity of the organosilicon compounds of the formula (II) used in the process of the invention is preferably from 0.6 to 10$^6$ mm$^2$/s, particularly preferably from 10 to 10$^4$ mm$^2$/s in each case at a temperature of 25° C.

Non-limiting examples of compounds of the formula (II) are α,ω-dihydroxydimethylpolysiloxane having a viscosity of 80 mm$^2$/s at 25° C., α,ω-dihydroxy-dimethylpolysiloxane having a viscosity of 20,000 mm$^2$/s at 25° C., α,ω-dichlorodimethylpolysiloxane having a viscosity of 40 mm$^2$/s at 25° C., α, ω-bis(trimethylsiloxy)-polymethylhydrogensiloxane having a viscosity of 25 mm$^2$/s at 25° C., α,ω-bis(trimethylsiloxy)polydimethyl-siloxane having a viscosity of 20 mm$^2$/s at 25° C., hexa-methyldisiloxane and 1,3-divinyl-1,1,3,3-tetramethyldi-siloxane.

Examples of compounds of the formula (III) are hexamethylcyclotrisiloxane, octamethylcyclotetra-siloxane and decamethylcyclopentasiloxane.

If X in the formula (II) is —OSiR$_3$, where R is as defined above, the corresponding compounds are organosilicon compounds which regulate the chain length.

Furthermore, it is possible, in the process of the invention, to use any organosilicon compounds which regulate the chain length and have also been able to be used in the previously known processes for equilibration and/or condensation in the presence of a catalyst based on phosphazene.

Such organosilicon compounds which regulate the chain length are preferably, apart from the compounds of the formula (II) where X is —OSiR$_3$, compounds of the formula $$R_2^3 \text{SiZ} \qquad (IV),$$

where

R$^2$ can be identical or different and are as defined for R, and

Z is a hydroxyl group, a radical —OR$^1$ where R$^1$ is a monovalent organic radical or a halogen atom.

Examples of radicals R$^2$ are the examples given for organic radicals R. Z is preferably a hydroxyl group, a chlorine atom, a methoxy radical or an ethoxy radical.

Non-limiting examples of compounds of the formula (IV) are trimethylchlorosilane and trimethyl-methoxysilane.

The amount of chain length-regulating organo-silicon compound used depends on the desired molecular weight of the organopolysiloxanes prepared by condensation and/or equilibration and is already known.

The organosilicon compounds used according to the invention are commercial products or can be prepared by methods customary in silicone chemistry. The individual constituents used in the process of the invention can in each case be one type of such constituents or a mixture of at least two types of such constituents.

In the process of the invention, the temperatures and pressures employed can likewise be the same as those used in the previously known processes for the equilibration and/or condensation of organosilicon compounds. The equilibration and/or condensation reactions of the invention are preferably carried out at from 50 to 200° C., particularly preferably from 80 to 160 ° C.

The equilibration and/or condensation reactions can be carried out at the pressure of the surrounding atmosphere, i.e. from 900 to 1100 hPa. To aid the removal of the elimination products formed in the condensation, for example water, HCl or alcohol, the equilibration and/or condensation of the organosilicon compounds is preferably carried out at a pressure of less than 80 kPa. However, the condensation and in particular the equilibration can also be carried out at higher pressures. The process of the invention can be carried out either batchwise or continuously.

After reaching the desired viscosity, the viscosity of the organosilicon compound obtained in the process of the invention can be kept constant by inhibition or deactivation of the catalyst used according to the invention, or rather of a reaction product which has been formed from the catalyst by reaction with an organosilicon compound to be condensed and/or equilibrated and likewise promotes the equilibration and/or condensation of organosilicon compounds. For inhibition or deactivation, inhibitors or deactivators may be added which have hitherto also been used in connection with phosphazenes, e.g. triisononylamine, n-butyllithium, lithium siloxanolate, aqueous ammonia, hexamethyldisilazane and magnesium oxide.

In order to ensure good dispersion of the components used in the process of the invention in one another, the mixture of these materials is preferably agitated while carrying out the process of the invention.

The organopolysiloxanes prepared according to the invention, in particular linear organopolysiloxanes, can be used for all purposes in which the linear organopolysiloxanes produced according to previously known processes by equilibration and/or condensation of organosilicon compounds have also been able to be used, for example for cleaners and polishes; cosmetic formulations; thread lubricants; for preparing organopoly-siloxane elastomers, where crosslinking can occur, depending on the terminal units of the linear organo-polysiloxanes, by condensation, by addition of Si-bonded hydrogen onto, for example, SiC-bonded vinyl groups, or by free radical formation; and for producing coatings which repel sticky materials.

The process of the invention for equilibrating and/or condensing organosilicon compounds has the advantage that it is simple to carry out and gives high yields. Furthermore, the process of the invention for equilibration and/or condensation has the advantage that equilibrium states are reached more quickly and/or achievement of equilibrium is possible using smaller amounts of catalyst.

The novel compositions which are derived from oxygen-containing phosphazenes and tertiary alcohols and promote equilibration and condensation processes display a very high activity and also have a shelf life of weeks. Furthermore, the compositions of the invention have the advantage that they are colorless to at most slightly yellow, and even after storage for weeks do not tend to darken.

In the examples described below, all parts and percentages are, unless otherwise indicated, by weight. Furthermore, all viscosity figures are based on a temperature of 25° C. Unless otherwise indicated, the following examples were carried out at the pressure of the surrounding atmosphere, i.e. about 1000 hPa, and at room temperature, i.e. at about 20° C., or at the temperature which is established on combining the reactants at room temperature without additional heating or cooling.

The oxygen-containing phosphazene A used in the following examples has the formula $PCl_3=N(-PCl_2=N)_n-PCl_2O$ where n is from 0 to 2, on average 1, and was prepared using the procedure described in Example 1 of U.S. Pat. No. 5,380,902 as cited at the outset.

EXAMPLE 1

66.7 g of oxygen-containing phosphazene A are placed in the reaction vessel under a nitrogen atmosphere.

100 g of tert-butanol are added dropwise while stirring to this phosphazene over a total period of 4 hours at such a rate that the internal temperature does not exceed 40° C. This gives 166 g of a clear, yellowish solution having a viscosity of 3.60 mm$^2$/s.

EXAMPLE 2

The procedure described in Example 1 is repeated, except that 100 g of tert-amyl alcohol are used in place of 100 g of tert-butanol. This gives 166 g of a homogeneous, slightly turbid solution having a viscosity of 11.25 mm$^2$/s.

EXAMPLE 3

100 g of tert-butanol are placed in the reaction vessel under a nitrogen atmosphere. 66.7 g of oxygen-containing phosphazene A are added dropwise while stirring to this alcohol over a total period of 4 hours at such a rate that the internal temperature does not exceed 40° C. This gives 166 g of a clear, yellowish solution having a viscosity of 11.29 mm$^2$/s.

EXAMPLE 4

50 g of 1,3-divinyltetramethyldisiloxane are equilibrated while stirring at 100° C., with 350 g of a methyl-terminated polydimethylsiloxane having a viscosity of 35 mm$^2$/s and 0.1 g of the solution obtained in Example 1. After 30 minutes, a viscosity of 8.9 mm$^2$/s is reached and this no longer changes even after a further 30 minutes (initial viscosity: 18.4 mM$^2$/s).

COMPARATIVE EXAMPLE 1

The procedure described in Example 4 is repeated, except that the catalyst used is not the solution obtained in Example 1 but instead a 40% strength solution of oxygen-containing phosphazene A in ethyl acetate. After 90 minutes, the viscosity has dropped to 17.4 mm$^2$/s. The siloxane mixture is not in equilibrium.

EXAMPLE 5

A mixture of 50 g of 1,3-divinyltetramethyl-disiloxane, 10 g of decamethylcyclopentasiloxane and 100 g of α,ω- dihydroxypolydimethylsiloxane having a viscosity of 20,000 mm²/s is equilibrated while stirring at 65° C. by addition of 28 μl of the solution obtained in Example 1. After 4 hours, a viscosity of 8.7 mm²/s is reached (initial viscosity: 740 mm²/s).

COMPARATIVE EXAMPLE 2

The procedure described in Example 5 is repeated, except that the catalyst used is not the solution obtained in Example 1 but instead a 40% strength solution of oxygen-containing phosphazene A in ethyl acetate. After 4 hours, a viscosity of 232 mm²/s is reached (initial viscosity: 740 mm²/s).

EXAMPLE 6

197 g of a methyl-terminated polydimethyl-siloxane having a viscosity of 10,000 mm²/s are equilibrated while stirring at 95° C. with 10 g of 1,3-divinyl-tetramethyldisiloxane with addition of 50 μl of the solution obtained in Example 2. After 25 minutes, a viscosity of 63.8 mm²/s is reached and this decreases only to 63.5 mm²/s after a further 15 minutes.

COMPARATIVE EXAMPLE 3

The procedure described in Example 6 is repeated, except that the catalyst used is not the solution obtained in Example 2 but instead a 40% strength solution of oxygen-containing phosphazene A in ethyl acetate. After 90 minutes, a viscosity of 240 mm²/s is obtained but equilibrium is not yet reached.

COMPARATIVE EXAMPLE 4

The procedure described in Example 1 is repeated, except that n-butyl alcohol is used in place of tert-butanol. Uncontrolled heating with evolution of HCl gas occurs. After addition of all the n-butyl alcohol used, phase separation occurs and highly polymeric, sparingly soluble materials are precipitated.

COMPARATIVE EXAMPLE 5

The procedure described in Example 1 is repeated, except that sec-butyl alcohol is used in place of tert-butanol. On cooling, sparingly soluble materials precipitate from the resulting solution.

What is claimed is:

1. In a process for equilibrating and/or condensing organosilicon compounds which are able to be equilibrated and/or condensed by contact with phosphazene-based catalysts, the improvement comprising selecting as said phosphazene-based catalyst, a composition obtained by mixing oxygen-containing phosphazenes with one or more tertiary alcohols at a temperature of from about 0° C. to about 70° C. and a pressure of from about 900 hPa to about 1100 hPa.

2. The process of claim 1, wherein the oxygen-containing phosphazenes are phosphazenes of the formula $$Y-PCl_2=N(-PCl_2=N)_n-PCl_2O \qquad (I),$$

where

Y is a chlorine atom or a hydroxyl group and;

n is 0 or an integer from 1 to 8, and/or their condensation products.

3. The process of claim 1, wherein n is 0 or an integer from 1 to 4.

4. The process of claim 1, wherein n is 0 or an integer from 1 to 3.

5. The process of claim 1, wherein said one or more tertiary alcohols have a pKa of greater than or equal to 18.

6. The process of claim 1, wherein said organosilicon compounds comprise one or more compounds of the formulae $$X(SiR_2O)_aSiR_2X \qquad (II)$$

and $$(SiR_2O)_b \qquad (III)$$

where R can be identical or different and are each a hydrogen atom or a monovalent, substituted or unsubstituted hydrocarbon radical, X can be identical or different and are each a hydroxyl group, a radical —OR¹ where R¹ is a monovalent organic radical, —OSiR₃ where R is as defined above or a halogen atom, a is 0 or an integer which is at least 1, and b is an integer from 3 to 12.

7. The process of claim 6, wherein a is from 2 to 500 and b is from 4 to 8.

8. The process of claim 6, wherein said organosilicon compounds of formulae II and III further comprise up to 5 mol percent based on diorganosiloxane groups, of $RSiO_{3/2}$ groups, $SiO_{4/2}$ groups, or both these groups.

9. The process of claim 1, wherein said tertiary alcohol comprises one or more tertiary alcohols selected from the group consisting of tertiary butanol, 1,1-dimethyl-1-propanol, 2,3-dimethyl-2-butanol, 2,3-dimethyl-2-pentanol, 1-methylcyclohexanol, 1-methylcyclopentanol, 2-methyl-2-hexanol, 2-methyl-2-pentanol, 2-methyl4-trimethylsilyl-2-butanol, 2-methyl-4-dimethylphenylsilyl-2-butanol and 2-phenyl-2-propanol.

10. The process of claim 1, wherein said composition is employed in an amount of from 0.1 to 1000 ppm by weight based on the weight of said organosilicon compounds.

* * * * *

UNITED STATES PATENT AND TRADEMARK OFFICE
CERTIFICATE OF CORRECTION

PATENT NO  : 5,994,490
DATED      : November 30, 1999
INVENTOR(S) : Benward Deubzer et al.

It is certified that error appears in the above-identified patent and that said Letters Patent is hereby corrected as shown below:

Column 10, Line 46, Claim 9, delete "2-methyl4-trimethylsilyl" and insert therefor --2-methyl-4-trimethylsilyl--.

Signed and Sealed this

Eighth Day of August, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO  : 5,994,490
DATED      : November 30, 1999
INVENTOR(S) : Bernward Deubzer et al.

It is certified that error appears in the above-identified patent and that said Letters Patent are hereby corrected as shown below:

Face page of patent, insert priority application number and priority date as --Federal Republic of Germany 19719340.4 filed May 7, 1997--.

Signed and Sealed this

Tenth Day of April, 2001

*Attest:*

NICHOLAS P. GODICI

*Attesting Officer*       *Acting Director of the United States Patent and Trademark Office*